United States Patent [19]

Birk et al.

[11] Patent Number: 4,992,092

[45] Date of Patent: Feb. 12, 1991

[54] METHOD FOR SAFENING GRAMINEOUS CROPS AGAINST PYRIDINE IMIDAZOLINONE HERBICIDES

[75] Inventors: Jeffrey H. Birk; Timothy Malefyt, both of Morrisville, Pa.

[73] Assignee: American Cyanamid Company, Stamford, Conn.

[21] Appl. No.: 292,209

[22] Filed: Dec. 30, 1988

[51] Int. Cl.$^5$ .................. A01N 43/40; A01N 43/00
[52] U.S. Cl. ........................... 71/92; 71/88; 71/112; 71/114
[58] Field of Search ............... 71/88, 92, 114

[56] References Cited

U.S. PATENT DOCUMENTS

| 3,564,768 | 2/1971 | Hoffman | 71/100 |
| 3,719,466 | 3/1973 | Ahle | 71/88 |
| 3,749,566 | 7/1973 | Hoffman | 71/100 |
| 4,638,068 | 1/1987 | Los | 71/94 |

OTHER PUBLICATIONS

Proceedings, North Central Weed Control Conference, Barrett et al., "Potential Safeners for Imazaquin", vol. 39, 1984, p. 39.

*Primary Examiner*—Glennon H. Hollrah
*Assistant Examiner*—Brian Burn
*Attorney, Agent, or Firm*—Alice C. Brennan

[57] ABSTRACT

The present invention provides a method for protecting a gramineous crop from injury caused by a pyridine imidazolinone herbicidal compound by applying to the crop a chemical safener in a non-phytotoxic antidotal amount.

8 Claims, No Drawings

METHOD FOR SAFENING GRAMINEOUS CROPS AGAINST PYRIDINE IMIDAZOLINONE HERBICIDES

BACKGROUND OF THE INVENTION

Pyridine imidazolinone compounds are members of a new class of potent herbicides that may be utilized at relatively low rates to effectively control a broad spectrum of undesirable weed species in agronomically important crops. This new class of compounds, and their use as herbicidal agents, is disclosed, respectively, in U.S. Pat. Nos: 4,638,068; 4,647,301; 4,650,514 and copending patent applications Ser. Nos. 850,192 filed on April 10, 1986 and 139,996 filed on Dec. 31, 1987.

The high potency of this new class of herbicides, though very advantageous for weed control at relatively low use rates, increases the possibility of injury to certain useful crop plants. The use of chemical safeners or antidotes to protect susceptible plants and plant seed from damage caused by sulfonyl urea herbicides is disclosed in U.S. Pat. No. 4,343,649.

1,8-Naphthalic anhydride may act as a safening agent for some cereal crops against injury from herbicides such as butylate, alachlor and molinate as described in U.S. Pat. Nos. 3,564,768; 3,749,566 and 3,719,466, respectively. Studies to determine the potential safening effect of 1,8-naphthalic anhydride and other safening agents on corn and sorghum against injury caused by imazaquin, a quinoline imidazolinone herbicide, have been published by M. Barrett in the Weed Science Society of America Abstracts, Volume 26, p. 77, (1986) and the North Central Weed Control Conference Proceedings, Volume 39, p. 39 (1984). In these studies, though safening was observed at low levels of herbicide applications, crop injury was still apparent when field use rates of herbicide were applied.

It is an object of this invention to provide a method to protect important crop plants from injury caused by pyridine imidazolinone herbicides by application of a chemical safener.

SUMMARY OF THE INVENTION

It has now been discovered that the range of agronomically important crops on which this new class of herbicides may be used can be significantly increased by applying a chemical safener selected from 1,8-naphthalic anhydride and the dicationic salt of 1,8-naphthalic acid, preferably the dipotassium salt of 1,8-naphthalic acid. The safener may be applied to the crop seed, to the soil surrounding the seed, to the foliage of the crop plant, or to the soil surrounding said plant. Gramineous crops such as corn, rice, wheat, sorghum, barley, oats, millet, rye, plant sugarcane and ratoon sugarcane may be protected from injury caused by the pre-emergence or postemergence application of pyridine imidazolinone herbicides by the application of 1,8-naphthalic anhydride as a seed coating or the dicationic salt of 1,8-naphthalic acid as an aqueous solution to be used as a spray alone or tank mixed for postemergent applications with said herbicide.

DESCRIPTION OF THE INVENTION

Pyridine imidazolinone herbicides of formula I

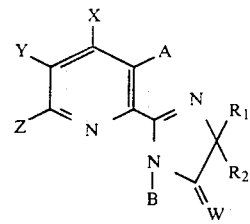

(I)

wherein $R_1$ is $C_1-C_4$ alkyl;

$R_2$ is $C_1-C_4$ alkyl or $C_3-C_6$ cycloalkyl; and when $R_1$ and $R_2$ are taken together with the carbon to which they are attached they may represent $C_3-C_6$ cycloalkyl optionally substituted with methyl;

A is $COOR_3$, $CONHR_6$, CHO, $CH_2OH$, $COCH_3$, $COC_6H_5$, CN, $CH_3$, CH=NOH, $CH_2COOH$, CONHOH, $CH_2CH_2COOH$, $CHR_8OH$,

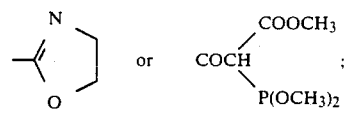

$R_3$ is hydrogen,
diloweralkylimino;
$C_1-C_{12}$ alkyl optionally substituted with one of the following groups: $C_1-C_3$ alkoxy, $C_1-C_3$ alkylthio, halogen, hydroxyl, $C_3-C_6$ cycloalkyl, benzyloxy, furyl, phenyl, halophenyl, loweralkylphenyl, loweralkoxyphenyl, nitrophenyl, carboxyl, lower-alkoxycarbonyl, cyano or triloweralkylammonium halide;
$C_3-C_{12}$ alkyl optionally substituted with one of the following groups: $C_1-C_3$ alkoxy, phenyl, halogen or loweralkoxycarbonyl or with two $C_1-C_3$ alkoxy groups or two halogen groups;
$C_3-C_6$ cycloalkyl optionally substituted with one or two $C_1-C_3$ alkyl groups;
$C_3-C_{16}$ alkynyl optionally substituted with one or two $C_1-C_3$ alkyl groups; or
a cation;

$R_6$ is hydrogen, hydroxyl, $C_3$-alkenyl, $C_3$-alkynyl or $C_1-C_4$ alkyl optionally substituted with one hydroxyl or one chlorine group;

B is H, $COR_4$ or $SO_2R_5$, provided that when B is $COR_4$ or $SO_2R_5$, A is $COOR_3$ in which $R_3$ is other than H, or a cation, $CH_3$ or CN; W is O; and Y and Z are not alkylamino, hydroxyl, or hydroxyloweralkyl;

$R_4$ is $C_1-C_{11}$ alkyl, chloromethyl or phenyl optionally substituted with one chloro, one nitro or one methoxy group;

$R_5$ is $C_1-C_4$ alkyl or phenyl optionally substituted with one methyl group;

W is O or S;

$R_8$ is $C_1-C_4$ alkyl or phenyl;

X is hydrogen, halogen, hydroxyl or methyl;

Y and Z are each hydrogen, halogen, $C_1-C_6$ alkyl, $C_1-C_4$ hydroxyloweralkyl, $C_1-C_6$ alkoxy, $C_1-C_4$ alkylthio, formyl, phenoxy, $C_1-C_4$ haloalkyl, nitro, cyano, $C_1-C_4$ alkylamino, di-$C_1-C_4$ loweralkylamino, $C_1-C_4$ alkylsulfonyl, difluoromethoxy, trifluoromethoxy, 1,1,2,2-tetrafluoroethoxy, phenyl optionally substituted with one $C_1-C_4$ alkyl, $C_1-C_4$ alkoxy or halogen;

$C_3$–$C_8$ straight or branched alkenyloxy optionally substituted with 1 to 3 halogens;

$C_3$–$C_8$ straight or branched alkylnyloxy optionally substituted with 1 to 3 halogen;

$C_2$–$C_6$ straight or branched alkenyl optionally substituted with phenyl, $C_1$–$C_4$ alkoxy or 1 to 3 halogens;

$C_2$–$C_6$ straight or branched alkynyl optionally substituted with phenyl, $C_1$–$C_4$ alkoxy, hydroxy, or 1 to 3 halogens;

$C_3$–$C_6$ cycloalkyl optionally substituted with methyl, halogen or $C_1$–$C_4$ alkoxy, and optionally interrupted by 1 oxygen, sulfur, amino, or $C_1$–$C_4$ alkylamino; oxiranyl optionally substituted by $C_1$–$C_4$ alkyl;

$C_1$–$C_4$ alkylcarbonyl optionally substituted with $C_1$–$C_4$ alkoxy or 1 to 3 halogens;

$C_1$–$C_4$ alkylcarbonylamino optionally substituted on nitrogen with $C_1$–$C_2$ alkyl or $C_1$–$C_4$ alkoxy and on carbon with $C_1$–$C_4$ alkoxy or 1 to 3 halogens;

$C_1$–$C_4$ alkylcarbonyloxy optionally substituted with $C_1$–$C_4$ alkoxy or 1 to 3 halogens;

$C_1$–$C_4$ alkyl substituted with one or more of the following groups:

$C_1$–$C_4$ alkoxy optionally substituted with phenyl, thienyl, furyl, cyclopropyl, tetrahydrofuryl, $C_1$–$C_4$ alkoxy, $C_1$–$C_4$ dialkylamino, $C_1$–$C_4$ alkylamino, $C_1$–$C_4$ trialkylammonium, or 1 to 3 halogens; with the proviso that when the substituent on the $C_1$–$C_4$ alkoxy group is $C_1$–$C_4$ alkoxy, $C_1$–$C_4$ alkylamino, $C_1$–$C_4$ dialkylamino, or $C_1$–$C_4$ trialkylammonium, the respective heteroatoms are separated by at least 2 carbon atoms;

$C_1$–$C_4$ alkenyloxy optionally substituted with 1 to 3 halogens;

$C_1$–$C_4$ alkynyloxy optionally substituted with 1 to 3 halogens;

$C_3$–$C_6$ cycloalkoxy;

phenylthio;

$C_1$–$C_4$ alkylthio optionally substituted with phenyl or 1 to 3 halogens;

$C_1$–$C_4$ alkylsulfinyl optionally substituted with phenyl or 1 to 3 halogens;

$C_1$–$C_4$ alkylsulfonyl optionally substituted with phenyl or 1 to 3 halogens;

$C_1$–$C_4$ alkylamino optionally substituted on carbon by phenyl or 1 to 3 halogens;

$C_1$–$C_4$ dialkylamino;

$C_1$–$C_4$ trialkylammonium;

$C_1$–$C_4$ alkylcarbonyloxy;

cyano;

phenylamino, optionally substituted in the ring by 1 to 3 halogens; $C_1$–$C_4$ loweralkyl or $C_1$–$C_4$ loweralkoxy;

phenoxy, optionally substituted in the ring by 1 to 3 halogens; $C_1$–$C_4$ loweralkyl, or $C_1$–$C_4$ loweralkoxy;

2(or 3)-furyl optionally substituted with halogen or $C_1$–$C_3$ alkyl;

2(or 3)-thienyl optionally substituted with halogen or $C_1$–$C_3$ alkyl;

N-methyl-2(or 3)-pyrrolyl:

hydroxy:

amino optionally substituted with $C_1$–$C_4$ alkoxy, $C_1$–$C_4$ alkylsulfonyl, $C_1$–$C_2$ alkyl and $C_1$–$C_4$ alkoxy, $C_1$–$C_4$ alkylsulfonyl and $C_1$–$C_4$ alkyl, amino, $C_1$–$C_4$ monoalkylamino, or $C_1$–$C_4$ dialkylamino:

2(or 4)-pyridyloxy optionally substituted with $C_1$–$C_4$ alkyl, trifluoromethyl or 1 or 2 halogens;

$C_1$–$C_4$ mono or dialkylaminocarbonylamino, optionally substituted on the nitrogen attached to the ring with $C_1$–$C_2$ alkyl or $C_1$–$C_4$ alkoxy;

$C_1$–$C_4$ alkoxycarbonylamino, optionally substituted on nitrogen with $C_1$–$C_2$ alkyl or $C_1$–$C_4$ alkoxy;

$C_1$–$C_4$ mono or dialkylaminocarbonyloxy;

the N-oxides thereof;

the optical isomers thereof when $R_1$ and $R_2$ are not the same;

the tautomers thereof; and the acid addition salts thereof except when $R_3$ is a cation;

may now be used to control a broad spectrum of weed species in the presence of gramineous crops such as corn, wheat, barley, rice, oats, millet, rye, sorghum, plant sugarcane and ratoon sugarcane by application of a safening agent as described herein More effectively, said gramineous crops may be protected against injury caused by the preemergence and postemergence application of compounds of formula I

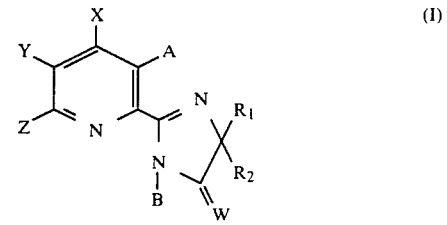

wherein A, B, W, $R_1$ and $R_2$ are as described hereinabove, X is hydrogen, Y and Z are each hydrogen, $C_1$–$C_6$ alkyl, amino, $C_1$–$C_4$ alkylamino, $C_1$–$C_4$ dialkylamino, $C_1$–$C_6$ alkoxymethyl, $C_1$–$C_6$ dialkoxymethyl, and $C_1$–$C_4$ alkylthiomethyl. Said crops may be safened by uniformly coating the crop seed with a non-phytotoxic antidotal amount of 1,8-naphthalic anhydride as a 5% to 50% wettable powder composition, preferably 20% to 40%, and planting the coated seed according to agronomic conventions. The above-said pyridine imidazolinone herbicides are then applied to the soil just before or after planting the thus-treated seed, but before the crop plants emerge. Pyridine imidazolinone herbicides such as 2-(4-isopropyl-4-methyl-5-oxo-2-imidazolin-2-yl)nicotinic acid;

5-methyl-2-(4-isopropyl-4-methyl-5-oxo-2-imidazolin2-yl)nicotinic acid;

5-ethyl-2-(4-isopropyl-4-methyl-5-oxo-2-imidazolin2-yl)nicotinic acid; and 5-(methoxymethyl)-2-(4-isopropyl-4-methyl-5-oxo-2-imidazolin-2-yl)nicotinic acid are examples of potent herbicides from which gramineous crops may be protected by the method of this invention.

Safening of gramineous crops from the post-emergence application of the above-described pyridine imidazolinone herbicides may be effected by allowing said crop plants to grow until the third to early fourth leaf stage, than spraying with an aqueous solution of the dicationic salt of 1,8-naphthalic acid at rates of about 0.5 kg/ha to 1.5 kg/ha, preferably 0.75 kg/ha to 1.0 kg/ha, either alone or tank mixed with the above-described pyridine imidazolinone herbicide.

Monocotyledonous crops, such as plant sugarcane and ratoon sugarcane, may be protected from injury caused by applications of pyridine imidazolinone total vegetation control agents, such as imazapyr, by uniformly coating seed pieces with 5% to 50% wettable powder compositions of 1,8-naphthalic anhydride or tank mixing an aqueous solution of the dipotassium salt of 1,8-naphthalic acid with the total vegetation control agent and spraying the foliage of the third to fourth leaf stage sugarcane plants, at rates of about 0.50 kg/ha to 1.5 kg/ha of safening agent to the crop plant.

A wide variety of troublesome weed species can be effectively controlled in the presence of important agronomic crops, such as corn, by safening the crop plants by uniformly coating the seeds with a 5% to 50% wettable powder composition of 1,8-naphthalic anhydride, planting the coated seed in the usual manner, and spraying the soil with a pyridine imidazolinone herbicide, such as imazethapyr, before the plants emerge; or by incorporating the herbicide into the soil before the coated seeds are planted.

In order to facilitate a more complete understanding of the invention, the following examples, are presented primarily for the purpose of illustrating more specific details thereof. The invention is not be limited thereby except as defined in the claims.

EXAMPLE 1

Evaluation Of The Method Of Application Of Naphthalic Anhydride, And The Safening Effects Thereof On Corn Against A Pyridine Imidazolinone Herbicide Mixtures of naphthalic anhydride and a wettable powder formulation containing 5% Marasperse CBO®, a sodium lignin sulfonate manufactured by Reed-Lignin, 1% Igepon T-77®, an N-methyl-N-oleoyltaurate manufactured by GAF Industries, and 94% Attaclay®, attapulgite fines manufactured by Englehardt are prepared and applied as a seed dust coating Seeds are coated at a rate of 2 grams of seed dust per 100 seeds.

Seed spray applications are prepared by suspending naphthalic anhydride in a mixture of 20% water and 80% acetone in sufficient quantity to provide the equivalent of from 1.0 kg-2.0 kg per hectare of compound to the exposed seed when applied through a spray nozzle operating at 40 psi for a predetermined time.

The pyridine imidazolinone herbicide is formulated as an aqueous concentrate composition containing the following:

| Component | wt/wt % |
|---|---|
| pyridine imidazolinone herbicide | 23.0 |
| acetic acid | 0.1 |
| ammonium hydroxide | 4.6 |
| (29% aqueous ammonia) | |
| urea | 20.0 |
| 30% silicon antifoam emulsion | 0.01 |
| water | 52.3 |

The pyridine imidazolinone composition is diluted with water in sufficient quantity to provide the equivalent of about 0.10 kg-0.075 kg/ha of herbicide to the soil when applied through a spray nozzle operating at 40 psi for a predetermined time.

Tank mix applications of naphthalic anhydride and the pyridine imidazolinone herbicide are achieved by adding sufficient naphthalic anhydride to the above described herbicidal dispersion to simultaneously provide from 0.5 kg-1.0 kg per hectare of the napthalic anhydride to the soil when said dispersion is applied through a spray nozzle operating at 40 psi for a predetermined time.

Corn seed are coated with seed dust containing from 6.25%-100% naphthalic anhydride as a wettable powder composition as hereinabove described. Coated and uncoated corn seeds are placed on sterilized Princeton soil in Jiffy flats at 3 seeds per cup. Each flat contains 12 cups and each treatment is applied to one flat.

A portion of the uncoated, exposed seed is treated with seed spray applications of naphthalic anhydride as described hereinabove.

All of the seeds are covered with 75 mL of soil and wetted down with water. The herbicide and herbicide plus naphthalic anhydride tank mix treatments are applied to the soil, and the flats are then placed on greenhouse benches, watered and cared for in accordance with conventional greenhouse procedures. From 4 to 5 weeks after treatment, the tests are terminated and each cup is examined and rated according to the rating system set forth below. The test results are averaged and recorded in Table I.

| Rating Scale | |
|---|---|
| Results of herbicide evaluations are expressed on a rating scale of 0-9. The scale is based upon a visual observation of plant stand, vigor, malformation, size, chlorosis and overall plant appearance as compared with a control. | |
| Rating  Meaning | % Control (Compared To Check) |
| 9  Complete Kill | 100 |
| 8  Approaching Complete Kill | 91-99 |
| 7  Good Herbicidal Effect | 80-90 |
| 6  Herbicidal Effect | 65-79 |
| 5  Definite Injury | 45-64 |
| 4  Injury | 30-44 |
| 3  Moderate Effect | 16-29 |
| 2  Slight Effect | 6-15 |
| 1  Trace Effect | 1-5 |
| 0  No Effect | 0 |

TABLE I

Evaluation Of The Safening Effects Of Naphthalic Anhydride On Corn Against The Preemergence Application Of A Pyridine Imidazolinone Herbicide

| Treatment | Rate kg/ha | Rating |
|---|---|---|
| 5-Ethyl-2-(4-isopropyl-4-methyl-5-oxo-2-imidazolin-2-yl)-nicotinic acid* | 0.100 | 8 |
| | 0.075 | 8 |
| Naphthalic Anhydride** | | |
| 100% Seed Dust | — | 1 |
| 75% Seed Dust | — | 1 |
| 50% Seed Dust | — | 0 |
| 25% Seed Dust | — | 0 |
| 12.5% Seed Dust | — | 0 |
| 6.25% Seed Dust | — | 0 |
| 100% NA Seed Dust and herbicide | 0.100 | 5 |
| 100% NA Seed Dust and herbicide | 0.075 | 5 |
| 75% NA Seed Dust and herbicide | 0.100 | 4 |
| 75% NA Seed Dust and herbicide | 0.075 | 4 |
| 50% NA Seed Dust and herbicide | 0.100 | 4 |
| 50% NA Seed Dust and herbicide | 0.075 | 3 |
| 25% NA Seed Dust and herbicide | 0.100 | 4 |
| 25% NA Seed Dust and herbicide | 0.075 | 2 |
| 12.5% NA Seed Dust and herbicide | 0.100 | 3 |
| 12.5% NA Seed Dust and herbicide | 0.075 | 1 |
| 6.25% NA Seed Dust and herbicide | 0.100 | 3 |
| 6.25% NA Seed Dust and herbicide | 0.075 | 1 |
| 2.0 kg/ha NA Seed Spray and herbicide | 0.100 | 5 |
| 1.0 kg/ha NA Seed Spray and herbicide | 0.100 | 6 |
| 0.5 kg/ha NA Seed Spray and herbicide | 0.100 | 6 |
| 2.0 kg/ha NA Tank Mix and herbicide | 0.100 | 5 |
| 1.0 kg/ha NA Tank Mix and herbicide | 0.100 | 8 |

TABLE I-continued

Evaluation Of The Safening Effects Of Naphthalic Anhydride On Corn Against The Preemergence Application Of A Pyridine Imidazolinone Herbicide

| Treatment | Rate kg/ha | Rating |
|---|---|---|
| 0.5 kg/ha NA Tank Mix and herbicide | 0.100 | 7 |

*Hereinafter noted as herbicide
**Hereinafter noted as NA (Safener)

EXAMPLE 2

Evaluation Of The Safening Effects Of Naphthalic Anhydride As A Coating For Crop Seed Against Preemergence Applications Of A Pyridine Imidazolinone Herbicide Mixtures of naphthalic anhydride and a wettable powder formulation containing 5% Marasperse CBO ® 1% Igepon T-77, and 94% Attaclay ® are prepared and applied as a seed dust coating. Seeds are coated at a rate of 2 grams of seed dust per 100 seeds.

Corn seed are coated with seed dust containing from 0.01%–10.0% naphthalic anhydride as a wettable powder composition as described above. Coated and uncoated corn seeds are placed on sterilized Princeton soil in Jiffy flats containing 12 cups per flat at 3 seeds per cup and one flat per treatment.

All of the seeds are covered with 75 mL of soil and then wetted down with water. The pyridine imidazolinone herbicide is formulated as described in Example 1, above, and diluted with water in sufficient quantity to provide the equivalent of from 0.10 kg–0.075 kg per hectare of active compound per cup. The treated flats are then placed on greenhouse benches, watered and cared for in accordance with conventional greenhouse procedures. From 4 to 5 weeks after treatment, the tests are terminated and each cup is examined and rated according to the rating system set forth above. The test results are averaged and recorded in Table II.

TABLE II

Evaluation Of The Safening Effect Of Naphthalic Anhydride As a Seed Dust Coating Against Preemergence Applications Of A Pyridine Imidazolinone Herbicide

| Treatment | Rate kg/ha | Rating |
|---|---|---|
| 5-Ethyl-2-(4-isopropyl-4-methyl-5-oxo-2-imidazolin-2-yl)-nicotinic acid* | 0.100 | 7 |
|  | 0.075 | 8 |
| 10% NA** Seed Dust and herbicide | 0.100 | 0 |
| 10% NA Seed Dust and herbicide | 0.075 | 0 |
| 1% NA Seed Dust and herbicide | 0.100 | 4 |
| 1% NA Seed Dust and herbicide | 0.075 | 2 |
| 0.01% NA Seed Dust and herbicide | 0.100 | 7 |
| 0.01% NA Seed Dust and herbicide | 0.075 | 5 |

*Hereinafter noted as herbicide
**Naphthalic anhydride

EXAMPLE 3

Evaluation Of The Safening Effects Of Naphthalic Anhydride On Corn Against The Preemergence Application Of Pyridine Imidazolinone Herbicides Corn seeds are coated with seed dust containing from 1%–20% naphthalic anhydride as a wettable powder composition as described in Examples 1 and 2, above. Coated and uncoated corn seeds are placed on sterilized Princeton soil in Jiffy flats containing 12 cups per flat at 3 seeds per cup and one flat per treatment.

All of the seeds are covered with 75 mL of soil and wetted down with water. After planting, the soil is sprayed with the selected aqueous solution containing a pyridine imidazolinone herbicide composition as described above in sufficient quantity to provide the equivalent of from 0.020 kg–0.100 kg per hectare of herbicidal compound per cup. Or, in the instance when the pyridine imidazolinone herbicide is an ester, the soil is sprayed with a 50/50 aqueous acetone mixture containing 0.5% TWEEN ® 20, a polyoxyethylene sorbitan monlaurate surfactant manufactured by Atlas Chemical Industries, and the pyridine imidazolinone herbicide in sufficient quantity to provide the equivalent of from 0.020 kg–0.100 kg/ha of herbicidal compound per cup. The treated flats are then placed on greenhouse benches as described above and evaluated at 4–5 weeks after treatment. The data obtained are averaged and shown in Table III below.

TABLE III

Evaluation Of The Safening Effects Of Naphthalic Anhydride On Corn Against The Preemergence Application Of Pyridine Imidazolinone Herbicides

| Herbicide | Rate kg/ha | % NA* Seed Dust | Rating |
|---|---|---|---|
| 5-Methyl-2-(4-isopropyl-4-methyl-5-oxo-2-imidazolin-2-yl)-nicotinic acid | 0.040 | — | 6 |
|  | 0.030 | — | 6 |
|  | 0.020 | — | 4 |
|  | 0.040 | 1 | 1 |
|  | 0.030 | 1 | 0 |
|  | 0.020 | 1 | 0 |
|  | 0.040 | 10 | 0 |
|  | 0.030 | 10 | 0 |
|  | 0.020 | 10 | 0 |
|  | 0.040 | 20 | 0 |
|  | 0.030 | 20 | 0 |
|  | 0.020 | 20 | 0 |
| Allyl 5-methyl-2-(4-isopropyl-4-methyl-5-oxo-2-imidazolin-2-yl)nicotinate | 0.100 | — | 8 |
|  | 0.075 | — | 6 |
|  | 0.050 | — | 2 |
|  | 0.100 | 1 | 2 |
|  | 0.075 | 1 | 1 |
|  | 0.050 | 1 | 1 |
|  | 0.100 | 10 | 2 |
|  | 0.075 | 10 | 0 |
|  | 0.050 | 10 | 0 |
|  | 0.100 | 20 | 1 |
|  | 0.075 | 20 | 0 |
|  | 0.050 | 20 | 0 |

*Naphthalic Anhydride

EXAMPLE 4

Evaluation Of Naphthalic Anhydride As A Safener Against The Preemergence Application Of A Pyridine Imidazolinone Herbicide In these tests naphthalic anhydride, as a technical grade material, is applied to the seed as a weight/weight % coating.

Naphthalic anhydride is mixed with 20 g portions of corn seed in sufficient quantities to provide from 0.25 to 1.0 weight/weight % of compound as a seed coating.

Coated and uncoated corn seeds are planted in jiffy flats at 3 seeds per cup and 12 cups per flat as described above. After planting, the soil is sprayed with the selected aqueous solution containing a pyridine imidazolinone herbicide composition as described in Example 1 in sufficient quantity to provide the equivalent of from 0.075 kg–0.100 kg per hectare of herbicidal compound per cup. The treated flats are then placed on greenhouse benches, watered and cared for in accordance with conventional greenhouse procedures. From 4–5 weeks after treatment, the tests are terminated and each cup is rated according to the rating system set forth above. The test results are averaged and reported in Table IV and Table V.

TABLE IV

Evaluation Of The Safening Effect Of Naphthalic Anhydride When Applied Directly To Corn Seed On A Weight/Weight % Basis Against Preemergence Applications Of A Pyridine Imidazolinone Herbicide

| Treatment | Rate kg/ha | Rating |
|---|---|---|
| 5-Ethyl-2-(4-isopropyl-4-methyl-5-oxo-2-imidazolin-2-yl)-nicotinic acid* | 0.100 | 8 |
|  | 0.075 | 7 |
| 1% by weight of Naphthalic Anhydride** | — | 1 |
| 0.5% by weight of NA | — | 1 |
| 0.25% by weight of NA | — | 0 |
| 1% by weight NA and herbicide | 0.100 | 3 |
| 1% by weight NA and herbicide | 0.075 | 2 |
| 0.5% by weight NA and herbicide | 0.100 | 3 |
| 0.5% by weight NA and herbicide | 0.075 | 1 |
| 0.25% by weight NA and herbicide | 0.100 | 2 |
| 0.25% by weight NA and herbicide | 0.075 | 1 |

*Hereinafter noted as herbicide
**Hereinafter noted as NA (Safener)

TABLE V

Evaluation Of The Safening Effect Of Naphthalic Anhydride When applied Directly To Corn Seed On A Weight/Weight % Basis Against Preemergence Applications Of A Pyridine Imidazolinone Herbicide

| Treatment | Rate kg/ha | Rating |
|---|---|---|
| 5-Ethyl-2-(4-isopropyl-4-methyl-5-oxo-2-imidazolin-2-yl)-nicotinic acid* | 0.100 | 7 |
|  | 0.075 | 6 |
| 0.25% by weight of Naphthalic Anhydride** | — | 0 |
| 0.15% by weight of NA | — | 0 |
| 0.10% by weight of NA | — | 0 |
| 0.05% by weight of NA | — | 0 |
| 0.25% by weight of NA and herbicide | 0.100 | 2 |
| 0.25% by weight of NA and herbicide | 0.075 | 2 |
| 0.15% by weight of NA and herbicide | 0.100 | 1 |
| 0.15% by weight of NA and herbicide | 0.075 | 1 |
| 0.10% by weight of NA and herbicide | 0.100 | 2 |
| 0.10% by weight of NA and herbicide | 0.075 | 1 |
| 0.05% by weight of NA and herbicide | 0.100 | 1 |
| 0.05% by weight of NA and herbicide | 0.075 | 2 |

*Hereinafter noted as herbicide
**Hereinafter noted as NA (Safener)

EXAMPLE 5

Evaluation Of The Safening Effects Of Naphthalic Anhydride On Wheat Against The Preemergence Application Of A Pyridine Imidazolinone Herbicide Winter wheat seeds are coated with a seed dust wettable powder formulation consisting of 5% Marasperse CBO ®, 1% Igepon T-77 ®, and 94% Attaclay ®, to which has been added from 1%-20% naphthalic anhydride. The seeds are coated at a rate of 2 grams of seed dust per 100 seeds.

Coated and uncoated winter wheat seeds are placed on sterilized Princeton soil in Jiffy flats containing 12 cups at 3 seeds per cup. The seeds are covered with 75 mL of soil and wetted down with water. After planting, the soil is sprayed with the selected aqueous solution containing a pyridine imidazolinone herbicide composition in sufficient quantity to provide the equivalent of from 0.050 kg-0.100 kg per hectare of herbicidal compound per cup. The treated flats are hen placed on greenhouse benches as described above and evaluated at 4-5 weeks after treatment. The test results are averaged and reported in Table VI.

TABLE VI

Evaluation Of The Safening Effects Of Naphthalic Anhydride On Winter Wheat Against The Preemergence Application Of A Pyridine Imidazolinone Herbicide

| Treatment | Rate kg/ha | Rating |
|---|---|---|
| 5-Ethyl-2-(4-isopropyl-4-methyl-5-oxo-2-imidazolin-2-yl)-nicotinic acid* | 0.100 | 9 |
|  | 0.075 | 8 |
|  | 0.050 | 6 |
| 20% Naphthalic Anhydride** Seed Dust | — | 0 |
| 10% NA Seed Dust | — | 0 |
| 5% NA Seed Dust | — | 0 |
| 1% NA Seed Dust | — | 0 |
| 20% NA Seed Dust and herbicide | 0.100 | 4 |
| 20% NA Seed Dust and herbicide | 0.075 | 4 |
| 20% NA Seed Dust and herbicide | 0.050 | 1 |
| 10% NA Seed Dust and herbicide | 0.100 | 6 |
| 10% NA Seed Dust and herbicide | 0.075 | 4 |
| 10% NA Seed Dust and herbicide | 0.050 | 1 |
| 5% NA Seed Dust and herbicide | 0.100 | 6 |
| 5% NA Seed Dust and herbicide | 0.075 | 6 |
| 5% NA Seed Dust and herbicide | 0.050 | 1 |
| 1% NA Seed Dust and herbicide | 0.100 | 8 |
| 1% NA Seed Dust and herbicide | 0.075 | 8 |
| 1% NA Seed Dust and herbicide | 0.050 | 7 |

*Hereinafter noted as herbicide
**Hereinafter noted as NA (Safener)

EXAMPLE 6

Evaluation Of The Safening Effects Of The Dipotassium Salt Of Naphthalic Acid Against The Postemergence Application Of A Pyridine Imidazolinone Herbicide Corn seeds (Pioneer 3475) are planted in 4 inch plastic pots using 3 seeds per pot with a greenhouse mix containing a loamy sand and 5% organic matter. The seeds are allowed to grow to the 3-4 leaf stage, and are then sprayed with an aqueous solution containing 0.5% TWEEN ® 20, the dipotassium salt of naphthalic acid (NAK) and a pyridine imidazolinone herbicide composition in sufficient quantities to provide 0.00 kg-1.00 kg/ha of NAK and from 0.05 kg-0.075 kg/ha of herbicide when applied to the plants with a 40 psi nozzle. After spraying, the plants are placed on greenhouse benches and are cared for in the usual manner. The plants are examined and rated according to the rating system provided at 2 weeks after treatment. The data obtained are recorded in Table VII, below.

TABLE VII

Evaluation Of The Safening Effects Of NAK When Applied As A Tank Mix Against The Postemergence Application Of A Pyridine Imidazolinone Herbicide

| Treatment | | Rating | | |
|---|---|---|---|---|
| NAK* kg/ha | Herbicide** kg/ha | I | II | III |
| — | 0.050 | 6 | 6 | 7 |
| 0.50 | 0.050 | 3 | 2 | 3 |
| 0.75 | 0.050 | 2 | 3 | 2 |
| 1.00 | 0.050 | 2 | 4 | 3 |
| — | 0.075 | 8 | 9 | 9 |
| 0.50 | 0.075 | 4 | 5 | 3 |
| 0.75 | 0.075 | 5 | 5 | 4 |
| 1.00 | 0.075 | 4 | 5 | 2 |

*Dipotassium salt of naphthalic acid
***5-Ethyl-2-(4-isopropyl-4-methyl-5-oxo-2-imidazolin-2-yl)nicotinic acid

EXAMPLE 7

Evaluation Of The Safening Effects Of Naphthalic Anhydride On Field Corn Against The Preplant Incorporation An Preemergence Applications Of Pyridine Imidazolinone Herbicides Fields in three separate regional locations in major corn producing areas are laid out in plots measuring 3.05×9.15 meters. Before planting, the soil is sprayed with selected aqueous solutions of pyridine imidazolinone herbicide compositions. Applications are made with a $CO_2$-powered sprayer. Test designs are replicated complete block designs with either three or four replicates. The test solutions applied provided the treated area with from 0.025 kg–0.200 kg/ha of a pyridine imidazolinone herbicide.

Field corn seeds (Pioneer 3475) are uniformly coated with wettable powder compositions containing from 20% to 40% naphthalic anhydride as described above. Coated and uncoated seeds are planted in early May in the treated plots. All trials are conducted using standard weed science procedures.

The treated plots are evaluated at intervals after planting and rated according to a safener rating scale of 0–100 with 0=no injury and 100=complete death. The data is averaged and reported in Table VIII.

Coated and uncoated field corn seeds (Pioneer 3475) as described above are planted in untreated 3.05×9.15 meter plots in the manner described above. After planting, the plots are sprayed with aqueous solutions of pyridine imidazolinone herbicide compositions in sufficient quantity to apply from 0.025 kg–0.200 kg/ha of herbicide to the soil.

The plots are evaluated as described above and the averaged data are reported in Table IX.

TABLE VIII

Evaluation Of The Safening Effects Of Naphthalic Anhydride On Corn Against The Preplant Incorporation Of Pyridine Imidazolinone Herbicides

| | | Safening Ratings At 4 Weeks After Planting | | | | | | | | |
|---|---|---|---|---|---|---|---|---|---|---|
| | | Location I % NA** Seed Dust | | | Location II % NA Seed Dust | | | Location III* % NA Seed Dust | | |
| Herbicide | Rate kg/ha | 0 | 20 | 40 | 0 | 20 | 40 | 0 | 20 | 40 |
| 5-Ethyl-2-(4-methyl- | 0.050 | 20 | 34 | 20 | 7 | 5 | 7 | 30 | 23 | 10 |
| 4-isopropyl-5-oxo- | 0.100 | 94 | 56 | 66 | 10 | 3 | 5 | 27 | 3 | 3 |
| 2-imidazolin-2-yl)- | 0.150 | 94 | 36 | 40 | 33 | 12 | 13 | 63 | 30 | 17 |
| nicotinic acid | 0.200 | 96 | 70 | 54 | 33 | 18 | 20 | 47 | 27 | 10 |
| 5-Methyl-2-(4-methyl- | 0.025 | 50 | 0 | 0 | 3 | 2 | 5 | 23 | 10 | 3 |
| 4-isopropyl-5-oxo- | 0.050 | 70 | 20 | 20 | 10 | 7 | 8 | 20 | 10 | 0 |
| 2-imidazolin-2-yl)- | 0.075 | 80 | 66 | 60 | 17 | 8 | 3 | 60 | 13 | 13 |
| nicotinic acid | 0.100 | 100 | 36 | 50 | 28 | 23 | 25 | 40 | 30 | 7 |

*Note: Incorporation of the herbicide at this location was poor due to heavy surface trash and the use of a field cultivator.
**Naphthalic Anhydride

TABLE IX

Evaluation Of The Safening Effects Of Naphthalic Anhydride On Corn Against The Preemergence Application Of Pyridine Imidazolinone Herbicides

| | | Safening Ratings At 4 Weeks After Planting | | | | | | | | |
|---|---|---|---|---|---|---|---|---|---|---|
| | | Location I % NA* Seed Dust | | | Location II % NA Seed Dust | | | Location III % NA Seed Dust | | |
| Herbicide | Rate kg/ha | 0 | 20 | 40 | 0 | 20 | 40 | 0 | 20 | 40 |
| 5-Ethyl-2-(4-methyl- | 0.050 | 40 | 6 | 14 | 3 | 2 | 3 | 20 | 20 | 10 |
| 4-isopropyl-5-oxo- | 0.100 | 64 | 6 | 20 | 8 | 3 | 3 | 23 | 10 | 3 |
| 2-imidazolin-2-yl)- | 0.150 | 60 | 14 | 20 | 25 | 5 | 5 | 63 | 30 | 17 |
| nicotinic acid | 0.200 | 76 | 26 | 26 | 23 | 3 | 7 | 67 | 43 | 20 |
| 5-Methyl-2-(4-methyl- | 0.025 | 14 | 0 | 6 | 0 | 0 | 0 | 7 | 7 | 0 |
| 4-isopropyl-5-oxo- | 0.050 | 54 | 6 | 6 | 7 | 2 | 2 | 27 | 7 | 7 |
| 2-imidazolin-2-yl)- | 0.075 | 66 | 26 | 40 | 3 | 0 | 3 | 47 | 30 | 10 |
| nicotinic acid | 0.100 | 80 | 20 | 46 | 23 | 5 | 3 | 53 | 17 | 10 |

*Naphthalic Anhydride

EXAMPLE 8

Evaluation Of The Safening Effects Of Naphthalic Anhydride On Sugarcane Against The Preemergence Application Of Pyridine Imidazolinone Herbicides Seed pieces of plant sugarcane are treated with naphthalic anhydride as a 20% wettable powder composition as described above by shaking in a covered container until seed pieces are uniformly coated. Treated and untreated seed pieces are planted in plots of 3×2 meters. Each plot contains 4 rows, 2 with treated seed pieces and 2 with untreated seed pieces. Test designs are modified randomized complete block designs with three replicates.

After planting, the plots are sprayed with aqueous solutions of pyridine imidazolinone herbicide compositions in sufficient quantity to apply from 0.3 kg to 0.6 kg/ha of herbicide to the soil. All trials are conducted using standard weed science procedures.

The plots are evaluated at 29 and 58 days after treatment (DAT) for crop safety and at 58 DAT for weed control. The results are averaged and reported in Table X.

| Plant Species Evaluated | |
|---|---|
| Common Name | Latin Name |
| SUGARCANE (PLANT) | SACCHARUM OFFICINARUM, L. |
| SIDA SP. | SIDA SP. |
| CRABGRASS, (HAIRY) LARGE | DIGITARIA SANGUINALIS, (L) |
| WEEDS, GENERAL | |

TABLE X

Evaluation Of The Safening Effect Of Naphthalic Anhydride On Sugarcane Against The Preemergence Application Of Pyridine Imidazolinone Herbicides

| | | | 29 DAT | 58 DAT | | | |
|---|---|---|---|---|---|---|---|
| | | | % Injury | % Injury | % Weed Control | | |
| Herbicide | Rate kg/ha | NA* 20% WP | Sugarcane (Plant) | Sugarcane (Plant) | Sida SP | Crab-grass | Weeds general |
| 2-(4-Isopropyl-4- | 0.30 | — | 60.0 | 73.3 | 98.3 | 100.0 | 99.7 |
| methyl-5-oxo-2- | 0.30 | + | 36.7 | 40.0 | 98.3 | 100.0 | 99.7 |
| imidazolin-2-yl)- | 0.60 | — | 73.3 | 90.0 | 100.0 | 100.0 | 100.0 |
| nicotinic acid | 0.60 | + | 43.3 | 71.7 | 100.0 | 100.0 | 100.0 |
| 5-Methyl-2-(4- | 0.30 | — | 50.0 | 66.7 | 100.0 | 100.0 | 100.0 |
| isopropyl-4- | 0.30 | + | 16.7 | 31.7 | 100.0 | 100.0 | 100.0 |
| methyl-5-oxo-2- | 0.60 | — | 66.7 | 90.0 | 100.0 | 100.0 | 100.0 |
| imidazolin-2-yl)- | 0.60 | + | 26.7 | 56.7 | 100.0 | 100.0 | 100.0 |
| nicotinic acid | | | | | | | |
| Control | 0.00 | — | 3.3 | 0.0 | 0.0 | 0.0 | 0.0 |
| | 0.00 | + | 0.0 | 0.0 | 0.0 | 0.0 | 0.0 |

*Seed pieces treated with naphthalic anhydride as a 20% wettable powder formulation are designated as (+). Seed pieces which are untreated are designated as (−)

EXAMPLE 9

Evaluation Of The Safening Effect Of Naphthalic Anhydride On Sugarcane Against the Postemergence Application Of Pyridine Imidazolinone Herbicides Ratoon sugarcane plants which have been grown to to the 4 leaf stage in 3×10 meter plots are sprayed with an aqueous suspension containing a 20% wettable powder formulation of naphthalic anhydride and a pyridine imidazolinone herbicide composition in sufficient quantities to provide from 0.0 kg–1.0 kg/ha of the naphthalic anhydride and from 0.15 kg–0.60 kg/ha of a pyridine imidazolinone herbicide to the plants. Test designs are modified randomized complete block designs with three replicates. All trials are conducted using standard weed science procedures.

The plots are evaluated at 16 and 60 days after treatment (DAT) for crop safety and at 60 DAT for weed control. The results are averaged and reported in Table XI.

| Plant Species Evaluated | |
|---|---|
| Common Name | Latin Name |
| SUGARCANE (RATOON) | SACCHARUM OFFICINARUM, L. |
| BEGGARTICK, HAIRY | BIDENS PILOSA, L. |
| TASSELFLOWER, RED | EMILIA SANCHIFOLIS (L.) |
| NUTSEDGE, PURPLE | CYPERUS ROTUNDUS |
| CRABGRASS, (HAIRY) LARGE | DIGITARIA SANGUINALIS, (L) |
| WEEDS, GENERAL | |

TABLE XI

Evaluation Of The Safening Effect Of Naphthalic Anhydride On Sugarcane Against The Postemergence Application Of Pyridine Imidazolinone Herbicides

| Treatment | | | 16 DAT | 60 DAT | | | | | |
|---|---|---|---|---|---|---|---|---|---|
| | | | % Injury | % Injury | % Weed Control | | | | |
| Herbicide | Rate kg/ha | NA* kg/ha | Sugarcane (Ratoon) | Sugarcane (Ratoon) | Beggar tick H | Tassel flwr R | Nuts edge P | Crab grass | Weeds general |
| 2-(4-Isopropyl-4- | 0.15 | 0.00 | 6.7 | 8.3 | 100.0 | 70.0 | 73.3 | 90.0 | 70.0 |
| methyl-5-oxo-2- | 0.15 | 1.00 | 13.3 | 3.3 | 100.0 | 70.0 | 83.3 | 90.0 | 80.0 |
| imidazolin-2-yl)- | 0.30 | 0.00 | 26.7 | 11.7 | 100.0 | 100.0 | 78.3 | 100.0 | 79.3 |
| nicotinic acid | 0.30 | 1.00 | 21.7 | 10.0 | 100.0 | 93.3 | 91.7 | 96.7 | 92.7 |
| | 0.60 | 0.00 | 36.7 | 20.0 | 100.0 | 100.0 | 95.0 | 100.0 | 95.0 |
| | 0.60 | 1.00 | 28.3 | 15.0 | 100.0 | 100.0 | 95.0 | 100.0 | 97.0 |
| 5-Methyl-2-(4- | 0.15 | 0.00 | 18.3 | 0.0 | 100.0 | 86.7 | 81.7 | 95.0 | 83.3 |
| isopropyl-4- | 0.15 | 1.00 | 11.7 | 0.0 | 100.0 | 100.0 | 88.3 | 95.0 | 93.3 |
| methyl-5-oxo-2- | 0.30 | 0.00 | 36.7 | 11.7 | 100.0 | 100.0 | 83.3 | 100.0 | 83.3 |
| imidazolin-2-yl)- | 0.30 | 1.00 | 26.7 | 6.7 | 100.0 | 100.0 | 95.3 | 100.0 | 95.3 |
| nicotinic acid | 0.60 | 0.00 | 43.3 | 16.7 | 100.0 | 100.0 | 95.0 | 100.0 | 96.0 |
| | 0.60 | 1.00 | 43.3 | 15.0 | 100.0 | 100.0 | 95.0 | 100.0 | 98.0 |
| Control | 0.00 | 0.00 | 0.0 | 0.0 | 0.0 | 0.0 | 0.0 | 0.0 | 0.0 |

*Naphthalic Anhydride

What is claimed is:

1. A method for protecting a gramineous crop from injury caused by a herbicidally effective amount of a pyridine imidazonlinone herbicide selected from the group consisting of 2(4-isopropyl-4-methyl-5-oxo-2-imidazolin-2-yl) nicotinic acid;

5-methyl-2-(4-isopropyl-4methyl-5oxo-2-imidazolin-2yl) nicotinic acid;

5-ethyl-2-(4-isopropyl-4-methyl-5oxo-2-imidazolin-2yl) nicotinic acid; and allyl 5-methyl-2-(4-isopropyl-4-methyl-5oxo-2-imidazolin-2-yl) nicotinate;

which comprises applying an effective non-phytotoxic antidotal amount of a chemical safener selected from the group consisting of 1.8-naphthalic anhydride and the dicationic salt of 1,8-naphthalic acid to the seed of the crop, the foliage of the crop, or the soil surrounding the crop or crop seed.

2. The method according to claim 1 wherein the safening agent is 1,8-naphthalic anhydride applied to the crop seed as a wettable powder composition.

3. The method according to claim 1 wherein the safening agent is the dicationic salt of 1,8-naphthalic acid applied to the crop seed, the soil surrounding the seed, the foliage of the crop, or the soil surrounding the crop as an aqueous solution.

4. The method according to claim 3 wherein the aqueous solution of the dipotassium salt of 1.8-naphthalic acid is applied at a rate of about 0.5 kg/ha to 1.5 kg/ha.

5. The method according to claim 1 wherein the crop is corn and the safening agent is 1,8-naphthalic anhydride applied to the crop as about a 5% to 50% wettable powder composition.

6. The method according to claim 1 wherein the crop is plant sugarcane and the safening agent is 1,8-naphthalic anhydride applied to the crop seed pieces as about a 5% to 50% wettable powder composition.

7. The method according to claim 1 wherein the crop is ratoon sugarcane and the safening agent is an aqueous solution of the dipotassium salt of 1,8-naphthalic acid applied at a rate of about 0.5 kg/ha to 1.5 kg/ha.

8. The method according to claim 1 wherein the crop is a monocotyledonous plant selected from the group consisting of corn, wheat, barley, oats, millet, rice, rye, sorghum, plant sugarcane and ratoon sugarcane.

* * * * *